United States Patent
Morrill et al.

(10) Patent No.: US 7,083,633 B2
(45) Date of Patent: Aug. 1, 2006

(54) ARTERIAL EMBOLIC FILTER DEPLOYED FROM CATHETER

(75) Inventors: Richard J Morrill, Billerica, MA (US); John R. Fagan, Pepperell, MA (US); David O. Williams, Barrington, RI (US)

(73) Assignee: Advanced Vascular Technologies LLC, Barrington, RI (US)

( * ) Notice: Subject to any disclaimer, the term of this patent is extended or adjusted under 35 U.S.C. 154(b) by 0 days.

(21) Appl. No.: 10/653,812

(22) Filed: Sep. 3, 2003

(65) Prior Publication Data

US 2004/0073253 A1   Apr. 15, 2004

Related U.S. Application Data

(60) Provisional application No. 60/453,244, filed on Mar. 11, 2003, provisional application No. 60/407,624, filed on Sep. 3, 2002.

(51) Int. Cl.
*A61M 29/00* (2006.01)
(52) U.S. Cl. ..................................... 606/200
(58) Field of Classification Search ................ 606/200, 606/198
See application file for complete search history.

(56) References Cited

U.S. PATENT DOCUMENTS

| | | | |
|---|---|---|---|
| 5,846,260 A | 12/1998 | Maahs | |
| 5,910,154 A | 6/1999 | Tsugita et al. | |
| 5,911,734 A | 6/1999 | Tsugita et al. | |
| 5,928,260 A * | 7/1999 | Chin et al. | 606/200 |
| 6,059,814 A * | 5/2000 | Ladd | 606/200 |
| 6,361,545 B1 | 3/2002 | Macoviak et al. | |

* cited by examiner

*Primary Examiner*—Michael Thaler
(74) *Attorney, Agent, or Firm*—Francis H. Kirkpatrick (57) ABSTRACT

An improved arterial catheter device for capturing emboli within the aorta and other arteries is described. The system typically includes an elongated catheter member bearing a filtration apparatus disposed at its the distal region, comprising a filter membrane and a mechanism for deploying and collapsing the filter. For reliable deployment, the deployment mechanism comprises at least one pair of struts, one being a compression strut and the other a tension strut. In use, the catheter is positioned so that the filter membrane is down stream from the possible embolic source and upstream from any vital organs of concern. When deployed the filter membrane will capture emboli from the blood stream, and upon filter removal will extract the emboli from the patient.

9 Claims, 6 Drawing Sheets

ARTERIAL EMBOLIC FILTER DEPLOYED FROM CATHETER

CROSS REFERENCE TO RELATED APPLICATIONS

This application claims the benefit of the priority of U.S. Ser. No. 60/407,624 filed Sep. 3, 2002, and of U.S. Ser. No. 60/453,244, filed Sep. 11, 2003.

1. Field of the Invention

This invention relates to improved methods and apparatus for capturing emboli within a blood vessel such as the aorta. More particular, it relates to a catheter with a mechanically deployable filter for capturing emboli dislodged during bypass surgery, thereby protecting the patient from the associated adverse effects. The device is characterized by using paired compression and tension struts for filter deployment. The struts are controllable from a proximal handle of the device.

2. Background of the Invention

Over recent decades tremendous advances have been made in the area of heart surgery, including such life saving surgical procedures as coronary artery bypass grafting (CABG) and cardiac valve repair or replacement. Cardiopulmonary bypass is an important enabling technology that has helped to make these advanced possible. However, there has been a growing awareness within the medical community and the patient population of the potential adverse effects of heart surgery and cardiopulmonary bypass surgery. Chief among these concerns is the potential of stroke or neurological deficit associated with heart surgery and cardiopulmonary bypass. One of the likely causes for stroke and neurological deficit is the release of emboli into the blood stream during heart surgery. Potential embolic material includes atherosclerotic plaque or calcified plaque from within the ascending aorta or cardiac valves and thrombus from within in the chambers of the heart. These potential emboli may be dislodged during surgical manipulation of the heart and/or the aorta, for example from cutting into the aortic wall to provide cannula access, or from the use of a cross clamp to block the connection of the aorta to the heart. In addition, the high velocity jetting effect from an aortic perfusion cannula may also cause dislodging of emboli. Air that enters the blood stream is another source of potential emboli. Emboli that flow to the brain may cause a stroke or neurological deficit. Clinical studies have shown a correlation between the number and size of emboli passing through carotid arteries and frequency and severity of neurological damage. At least one study has found that strokes seem to be associated with macroemboli larger than approximately 100 micrometers whereas emboli of approximately 100 micrometers or smaller cause more subtle neurological deficits. A method of capturing and removing these emboli would be very beneficial to reduce the potential of such embolic events.

Several medical articles have been published relating to cerebral embolic events and adverse cerebral outcomes associated with bypass surgery, including Roach et al, New England Journal of Medicine, vol. 335 No 25 1996 pp. 1857–1863; and Barbut et al, Stroke vol. 25 pp. 2398–2402, 1994.

There are many concepts and deployment mechanisms for embolic filtering in the coronaries and carotid arteries. Currently, there are three basic concepts disclosed for an aortic filter, i.e., a cone shape, a parachute shape, and a "fish net" structure. Typically, the fish net is attached to a simple hoop, and the hoop enters the artery in a perpendicular fashion, i.e. edgewise. The cone is typically attached to a wire frame, while the parachute may or may not have a wire frame and is tethered to the deployment shaft.

There is also passive and active deployment. In passive deployment, the filter mouth is preloaded to spontaneously open, customarily using a sleeve to keep it closed or collapsed. When the sleeve is pulled back, the spring loaded wire frame opens. Another form of passive deployment requires that blood flow and subsequent pressure drop across the filter will force the filter open, similar to the action of a parachute. Examples of the active deployment systems are an annular shaped balloon attached to the mouth of the filter, and a hollow hoop with a stiffening rod to open the hoop.

These designs have some disadvantages. First, there is a possibility that they may not form a tight seal against the aortic wall due to blood flow following the path of least resistance and flowing around the filter, between the filter and the arterial wall, thus possibly allowing emboli to escape downstream. Another disadvantage is that the deployment mechanism and/or the filter itself once positioned (for example perpendicular to the aorta) may occupy the same space as the heart pump cannula, thus causing the two to bump into each other, or to be incorrectly oriented.

The fish net design is currently the only commercially available device for filtering emboli during bypass surgery. As described in Maahs (U.S. Pat. No. 5,846,260), this filter is attached to the heart-lung machine cannula. The filter is configured in such that the filter is located upstream from the cannula outlet, i.e., between the aortic clamp and the cannula. This provides no embolic protection caused for the output of the cannula and no protection during placement of the cannula. This filter provides protection only during manipulation of the clamp.

Tsugita (U.S. Pat. No. 5,910,154) discloses various filter designs. The basic premise of these designs is a passive method of a spring-loaded open wire frame with a filter attached, mounted on a guide wire. The filters are deployed in either a cone or a parachute configuration. The wire frame is collapsed or constrained using a sheath, which slides over the filter to collapse it for insertion or removal. The wire frame opens when a restraining sheath is pulled back.

Tsugita (U.S. Pat. No. 5,911,734) discloses a cone shape filter design using an active deployment method, i.e., an annular shaped balloon.

Macoviak (U.S. Pat. No. 6,361,545) discloses a perfusion catheter with an embolic filter attached. They disclose both passive and active deployment methods. The passive method relies on the spring tension of the hoop and the flow of the blood to open the filter. The active method uses a hoop made of a hollow material, which is made stiffer with some means such as a stiffening rod or hydraulic pressure.

SUMMARY OF THE INVENTION

The improved embolic filter has more efficient and predictable deployment mechanisms for the filter. These allow capture of emboli both from a perfusion cannula and from a clamped arterial segment, for example during cardiac bypass surgery. One source of improvement is the use of paired struts, one a compression strut and the other a tension strut, for deployment of the membrane. Deployment is achieved directly by a multiplicity of strut pairs, or by the strut driven deployment of a hoop bearing the filtration membrane. The struts are optionally provided with living hinges.

In one aspect, the invention comprises an embolic filter deployed from a catheter, wherein the means of deployment comprise a first, outer catheter tube having a distal portion to which is attached a distal end of an embolic filter and to which tube are also attached one or more tension struts; a second, middle catheter tube or wire, to which are attached one or more compression struts, and wherein each compression strut is also attached to a corresponding tension strut; and a third, inner catheter tube or wire to which are connected means for operably connecting the tip region of the tube or wire and the open, distal edge of the embolic filter. The means provide a way to open or close the open edge of the filter membrane to deploy the embolic filter into an open position by the action of the compression struts on the tension struts, when the outer tube and the inner tube or wire are both moved proximally with respect to the middle tube or wire.

In a first embodiment, the filter deployment means comprise at least three pairs of compression and tension struts, and preferably six to ten pairs of struts. The filter is retained in position by a set of tethers attached to the inner tube or wire. In a second embodiment, which is presently preferred, the deployment means comprises at least one pair of struts, respectively connected to the middle tube or wire and to the outer tube or to a wire. The other ends of the struts are connected to a flexible hoop, which is also operatively connected to an attachment device or region neat the tip of the inner tube. In either embodiment, the struts may be connected to each other, or to other components, either directly, or via a hinge, which may be a living hinge. In the second embodiment, the open end of the filter is attached to the hoop, and the hoop is deployed by using the struts to push the hoop radially against the wall of the artery, eventually forming a seal against the arterial wall. When multiple struts are used, the strut pairs force the membrane out radially by direct contact.

The deployment method is an important advance. The action of the paired struts is far superior to the action of a single strut, because when a pair of struts is connected distally, the distal movement of the proximal end of the inner strut (the compression strut) will bend the outer strut (the tension strut) outward. The paired struts are a simple and reliable way of achieving this action at the far end of a catheter.

BRIEF DESCRIPTION OF THE FIGURES

FIG. 6 shows three steps in the deployment of the device of FIG. 5 inside an aortic arch.

DETAILED DESCRIPTION OF THE INVENTION

In the description below, the words "membrane", "filter", and "filter membrane" are used interchangeably to denote the filtration element of the device. This element is typically composed of a wire or plastic mesh or cloth. It preferably has some stiffness, but is sufficiently flexible to smoothly deploy and later collapse into a configuration for removal. The holes in the cloth or mesh should be large enough to allow the passage of blood, including blood cells, with low pressure drop and with minimal hemolysis or cell destruction. Numerous potentially suitable filter membranes are known, and can be selected to permit high flow while retaining potentially embolic materials.

The words "embolic" and "emboli" are used herein to denote potentially embolus-causing materials. In practice, such materials comprise clots or thrombi, loosened pieces of atherosclerotic plaque, tissue fragments, and materials aggregated by the effects of shear or other disruption during the use of a heart-lung machine or other blood contacting devices.

The description is focused on a preferred embodiment, which is blood filtration within the aorta. The invention is also applicable in other arteries, and in large veins (e.g., the vena cava), and references to the "aorta" will generally apply to all blood vessels requiring blood filtration, except where clearly specific to the particular anatomy of the aorta.

The embolic filter of the present invention takes the form of an elongated tubular member or catheter having an embolic filter assembly mounted at the distal end. The elongated tubular catheter shaft is adapted for introduction into a patient's aorta or other artery via a peripheral artery approach. The embolic filter assembly in its undeployed state is closely wrapped and/or compressed around the catheter shaft. In a deployed state, the filter expands to the approximate size of the aorta. A pair of struts or a series of pairs of struts, each pair comprising a tension strut and a compression strut, optionally in cooperation with a hoop, expands the filter. During deployment, the compression strut bends as it pushes on the distal end of the tension strut, thus deflecting the tension strut in an outward direction (radially) from the shaft. In turn, the deflected strut or struts deploys the filter membrane, either directly, or via the displacement of a hoop.

The struts are typically connected with a hinge, which in some embodiments is preferably a "living" hinge. A living hinge is a thin section of material that connects two thicker segments of a part. It keeps them together and allows the part to easily flex at the living hinge point. A familiar example of such a hinge is the flip top cover of a squeeze bottle of ketchup In embodiments using a hoop to deploy the filter, the hoop is sized so that it is slightly larger in diameter than the aorta or other artery. Then, when the hoop is deployed, it will be stopped at some angle less than perpendicular to the local axis of the aorta. The operator is able to adjust or modify the amount of engagement of the hoop to the aortic wall by changing the angle of the hoop relative to the aorta, since the more perpendicular the hoop is to the aorta, the tighter the seal of the filter to the aorta will be. A further benefit of this deployment system is that it allows more room for the heart pump cannula to be placed without interference with the filter, and for the filter to be upstream of all organs. i.e., to be in between the body's vital organs and the potential embolic source.

An outer sheath or tube may be used when the filter is in the collapsed state to prevent bunching of the membrane during insertion and removal. Radioopaque markers and or sonoreflective markers may be located on the catheter and or filter assembly.

In order to provide sufficient flow of oxygenated blood to the body through the filter without excessive pressure drop, it is preferred that the surface area of the filter mesh be at least twice the luminal area of the aorta. However, the exact ratio is not critical.

In use in coronary bypass surgery or in coronary valve replacement, the embolic filter is inserted into the patient's aorta in the collapsed state via a peripheral artery approach. The filter assembly is advanced over the arch and into in the ascending aorta. The filter assembly is then positioned so that the filter opening is proximal to the innominate artery and the filter is then deployed. The positioning of the filter assembly and its condition in the deployed state can be monitored using transesophageal echography (TEE), ultrasound, or fluoroscopy. (Appropriate markers for such techniques may be affixed to the device.) Then the heart-lung perfusion cannula can be positioned, and the bypass procedure can continue using normal and accepted procedural protocols. The embolic filter will now prevent emboli from passing either from the operating zone, or from the heart-lung machine, to any vital organs. At the end of the procedure, the filter is collapsed, capturing any emboli. Both struts then pull on the hoop to help collapse it, and it is withdrawn from the patient.

FIRST EMBODIMENT

Figure 1:
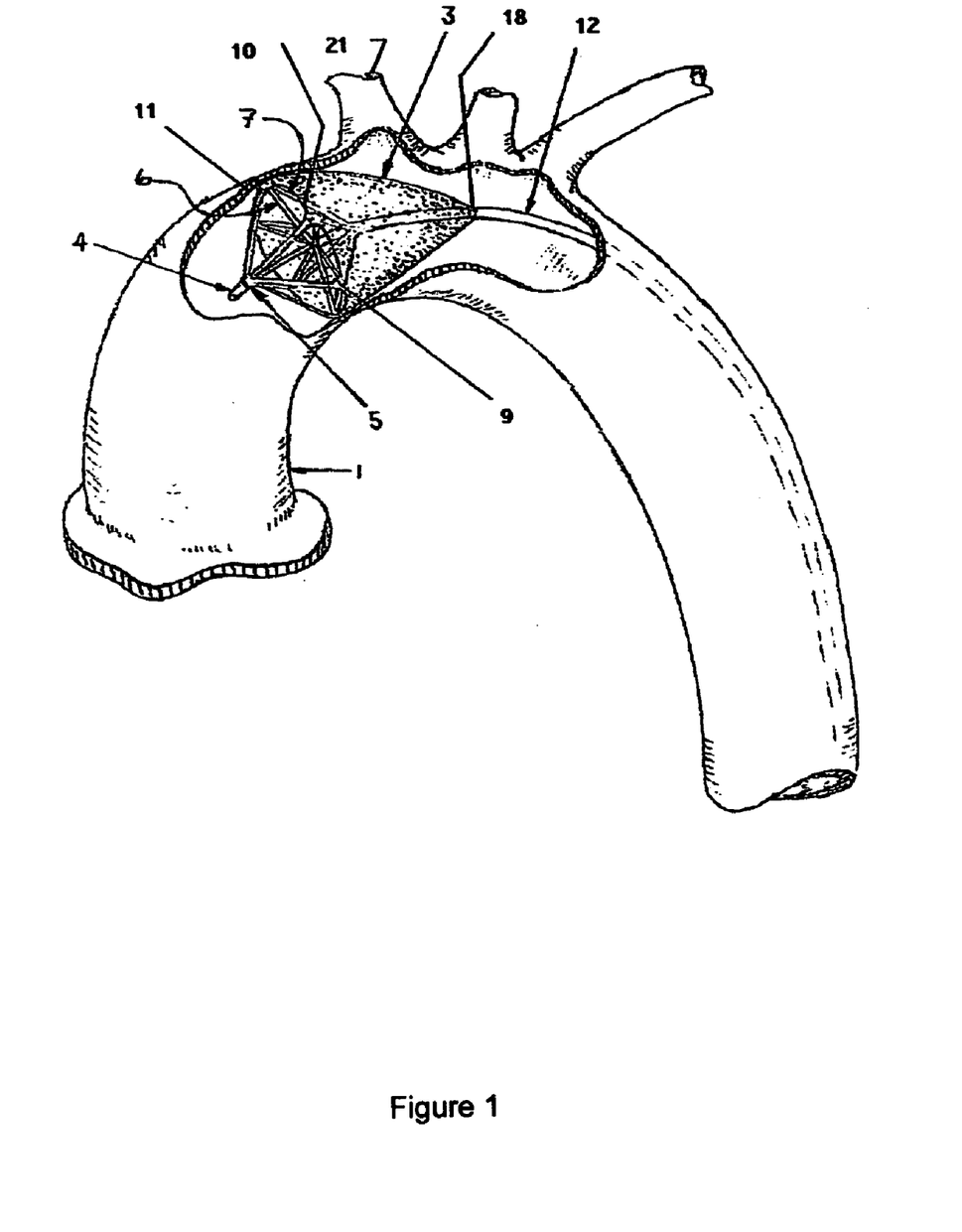
FIG. 1 shows a multi-strut filter concept deployed in an aorta.

Several embodiments of the invention are described, with reference to the figures. A first embodiment is shown in FIG. 1, showing a filter deployed within an aorta 1. The catheter system includes three concentric flexible elongated members 12, 13, and 14 having a distal region adapted to enter an artery, and a proximal region extending through the vasculature and eventually outside the body. The catheter system includes a filtration membrane 3, which is lightly stippled in the illustration. The filter has an expansion means, typically comprising several pairs of compression 6 and tension 7 struts disposed about the distal region of the flexible elongated member 12. The system as illustrated has four strut pairs, and might have as few as three, but preferably has six or more preferably eight pairs, to obtain good approximation of the edges of the filter 3 to the wall of the artery 1. When deployed, the distal regions of the struts 6 and 7 are deflected outward from the distal portion of member 12 to some distance from the distal shaft. Tip 4, marker band 5, distal membrane edge 10, proximal membrane attachment 18, and the innominate artery 21 are also noted.

Figure 2:
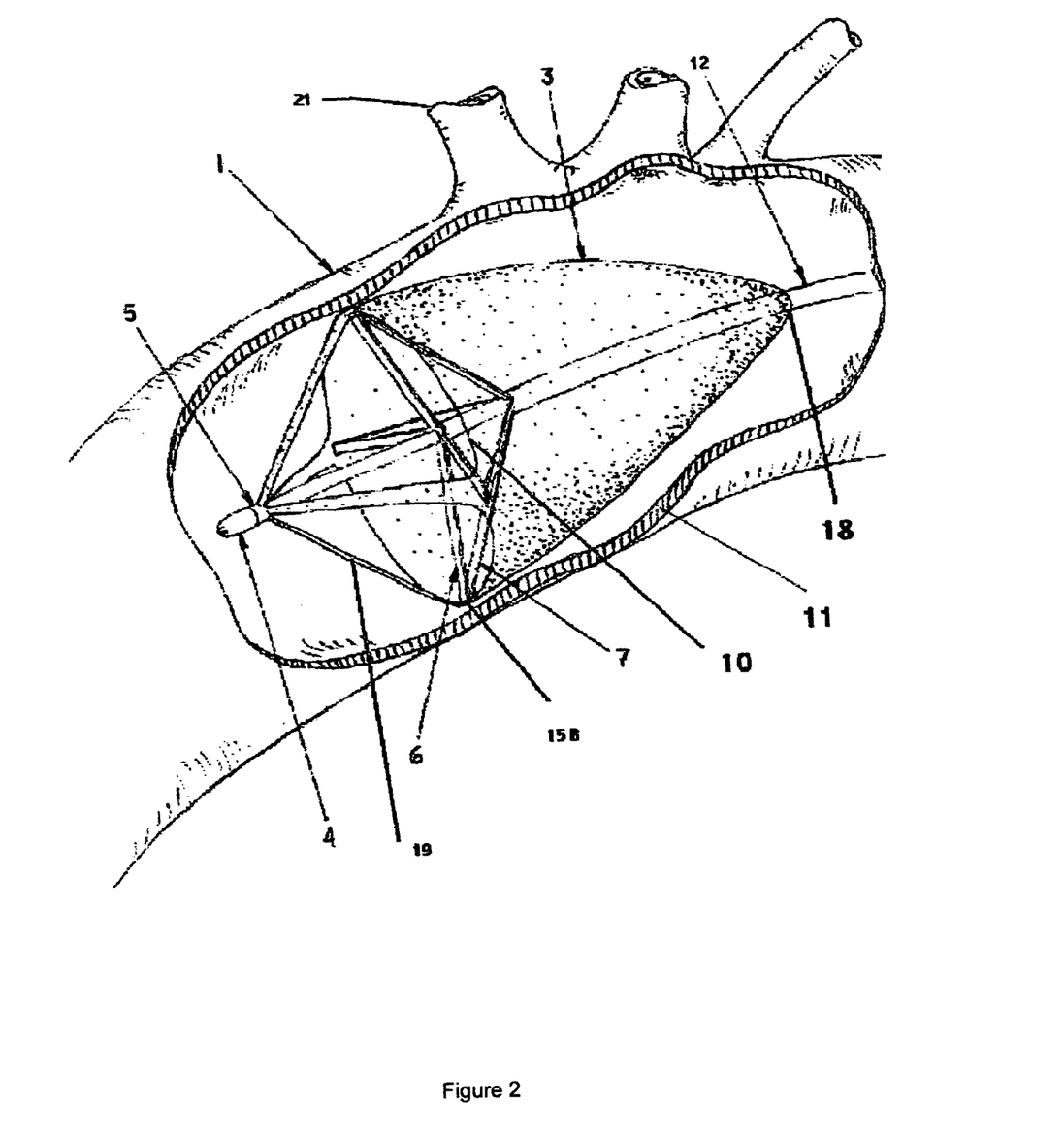
FIG. 2 shows an enlarged view of the filter deployed within the aorta.

A magnified view of the filter catheter system is depicted in FIG. 2. The membrane 3 can be seen to connect at its proximal end 18 with outer catheter tube 12. The distal, open edge 10 of the membrane 3 is operably connected to the distal end of an elongated tube 14 at its tip 4 via a series of tethers 19. The position of the open edge 10 of the filter 3 lies approximately at the region of the hinges 15B between the struts 6 and 7. Since the struts and the tethers are under tension in the deployed state, attachment of edge 10 to the struts or other structure is possible but not normally required.

Figure 3:
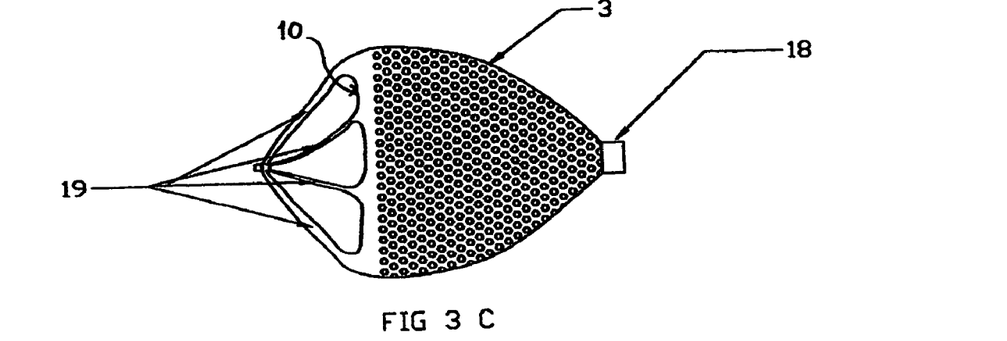
FIG. 3A shows the deployment mechanism with multiple pairs of tension and compression struts in the deployed position, connected with a living hinge.
FIG. 3B shows the deployment mechanism with the pairs of tension and compression struts in the collapsed position, connected with a living hinge.
FIG. 3C shows the filter membrane as it is configured in the deployed state.

FIG. 3 is a more detailed view of the same embodiment. FIG. 3C (top) shows the filtration membrane 3 in its expanded state, including the proximal end 18 of the membrane 3, which is bonded by any suitable means to the distal end segment 12 of the outer catheter tube. Suitable bonding means include without limitation adhesives, hot melting, shrink-wrap bands, and mechanical clips. Also shown is open distal edge 10 of the membrane. Several tethers 19—in this illustration 4—extend from the distal edge 10 of the membrane 3 and are affixed to the tip 4, as shown in FIG. 2, by any convenient means.

FIG. 3A (center) shows the deployed state of the filtration apparatus, with the membrane removed for clarity. The tension struts 7 are attached to the distal region of tube 12, also by adhesives, clips, melt bonds, etc. The tension struts 7 may have a hinge 15 in the region where they join tube 12. The hinge, as illustrated, is a living hinge, although other hinge forms are suitable and in fact, a specific hinge may not be needed if the struts bend elastically.

Emerging from outer shaft or tube 12 is a middle tube 13. The compression struts 6 are attached to middle tube 13, in the same general manner as the tension struts 7 are attached to outer tube 12, and likewise may optionally have a hinge or hinge region 15A. The struts 6 and 7 are joined at their distal ends, in this embodiment preferably by a third hinge 15B.

Emerging from middle tube 13 is inner tube 14. Tube 14 carries a tip 4, which may be adapted to help in threading the catheter through the arteries, and which may contain an outlet hole for passage of a guidewire (not illustrated). Tube 14 may also carry a marker 5 to allow detection of its position by fluoroscopy, ultrasound, or other location techniques. Similar markers may be carried on other parts of the device, particularly near proximal membrane attachment 18 (not illustrated.). The tethers 19 (not shown in this view) support the membrane, and maintain it in a position where the membrane can be expanded or collapsed by the action of the struts 6 and 7.

FIG. 3B shows the mechanism in its collapsed position. Key parts are numbered the same as in FIG. 3A. In the collapsed position the struts 6 and 7 and the membrane 3 (rendered transparent, and visible as a single line above and below the struts, running from the tip 4 to the proximal region 18), can be inserted into an arterial vessel and positioned to a region of interest, such as the ascending aorta. Likewise, after use for collecting emboli, the struts are collapsed, returning the device to the configuration of FIG. 3B so that it can be removed.

OPERATION OF THE DEVICE

The membrane is deployed by changing the relative positions of the three catheter tubes 12, 13 and 14. Once the device has been placed in the appropriate region of the artery, for example as shown in FIG. 1 and FIG. 2, then inner tube 14 is retracted proximally with respect to middle tube 13. This loosens the tethers and allows the membrane to expand. Next, the outer tube 12 is moved proximally with respect to middle tube 13 (Compare FIG. 3A with FIG. 3B). This proximal movement bows the compression strut 6, as shown in FIG. 3A, and this in turns forces tension strut 7, and thus the hinge region 15B between struts 6 and 7, to move in a radial (outward) direction. This expands the open edge 10 of the membrane. Eventually the outward expansion contacts the interior wall of the aorta (not shown), thereby positioning the open edge 10 of the membrane 3 against or near the arterial wall. The inner tube 14 optionally may then be moved distally with respect to tube 13 to tighten the tethers, to prevent backward slipping of edge 10; or, the right amount of slack in the tethers can be created by initially displacing the tube 14 proximally by a predetermined distance.

When removing the device, it is preferable to move inner tube 14 distally while outer tube 12 is being moved distally to collapse the pairs of struts. This will tend to keep the membrane edge 10 from moving backward with respect to the struts, and will tend to confine any captured emboli to the region near the proximal end 18 of the membrane filter 3. Optionally, a sheath (not shown) can be positioned over the apparatus distal to tube 12 to retain the components in position during retraction, and/or during insertion as well.

ALTERNATIVES

Several alternatives are possible in the construction of the first embodiments. Clearly, there need to be several pairs of struts 6 and 7 to make a reasonably uniform expansion of the membrane 3. Three pairs is minimal; four pairs, as illustrated, is better; five or six pairs is better yet; and about eight pairs is believed to be approximately the optimum tradeoff between mechanical complexity and goodness of fit to the arterial wall, to prevent blood flow from bypassing the filter. In addition, several components can be replaced with wires extending from the operating region to the proximal controls. First, the tube 14 can be replaced by a wire, running in tube 12 or tube 13. If a guidewire is needed, it likewise can run in tube 12 or 13. Second, in addition or alternatively, tube 13 could also be replaced by a wire. Thus, a configuration could be used in which there was only one tube, 12, to which the tension struts 7 are glued; and the tube 12 would contain a wire analogous to tube 13, a wire analogous to tube 14, and optionally a guidewire.

Also, the deployment has been described in terms of particular relative movements. It would be equivalent to describe the relative motions as a movement of tube 14 proximally with respect to tube 12, and a move of tube 13 proximally vs. 12 as well.

SECOND EMBODIMENT

Figure 4:
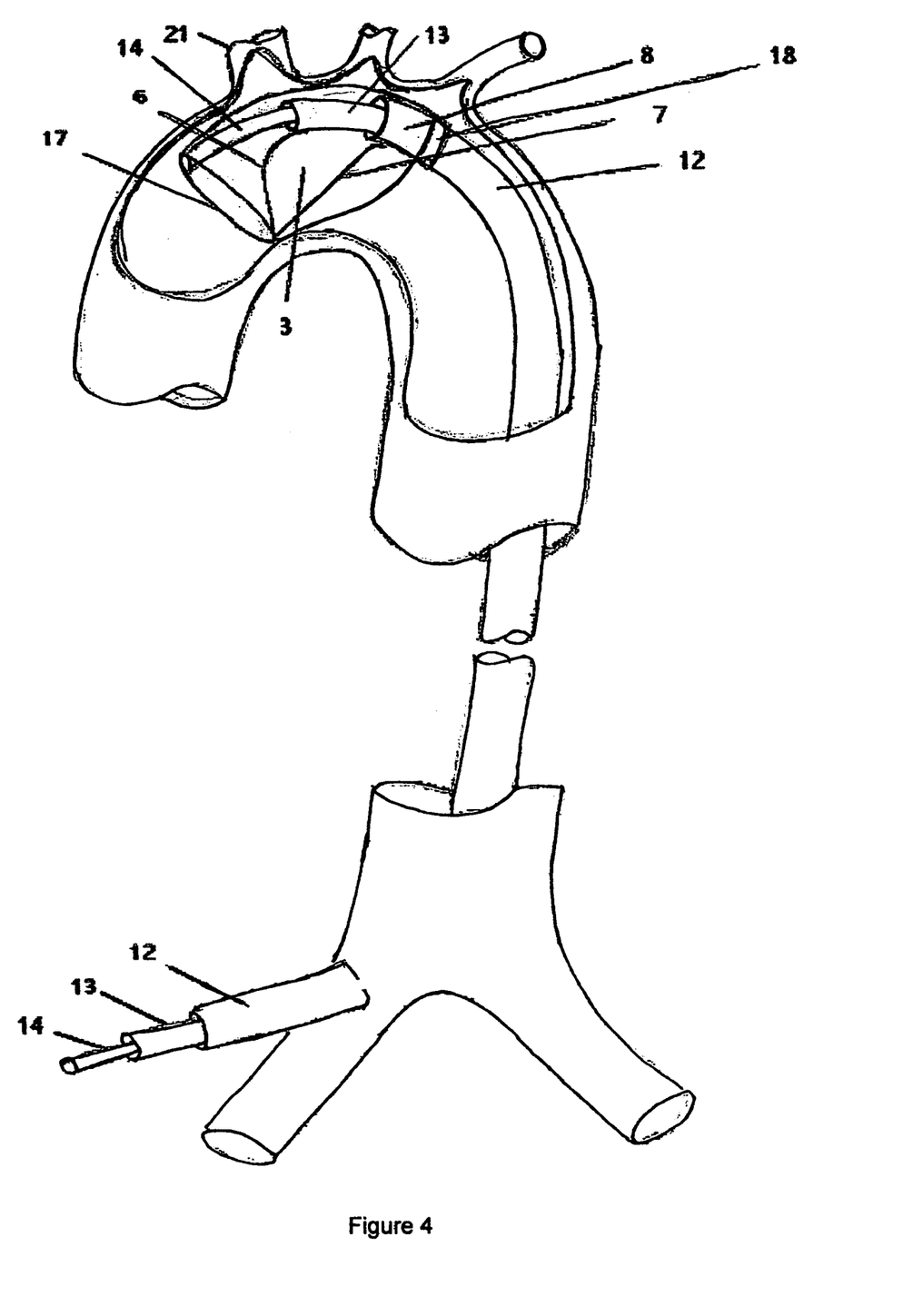
FIG. 4 shows an alternative embodiment with a single pair of compression and tension struts deploying a hoop in the aorta.
Figure 5:
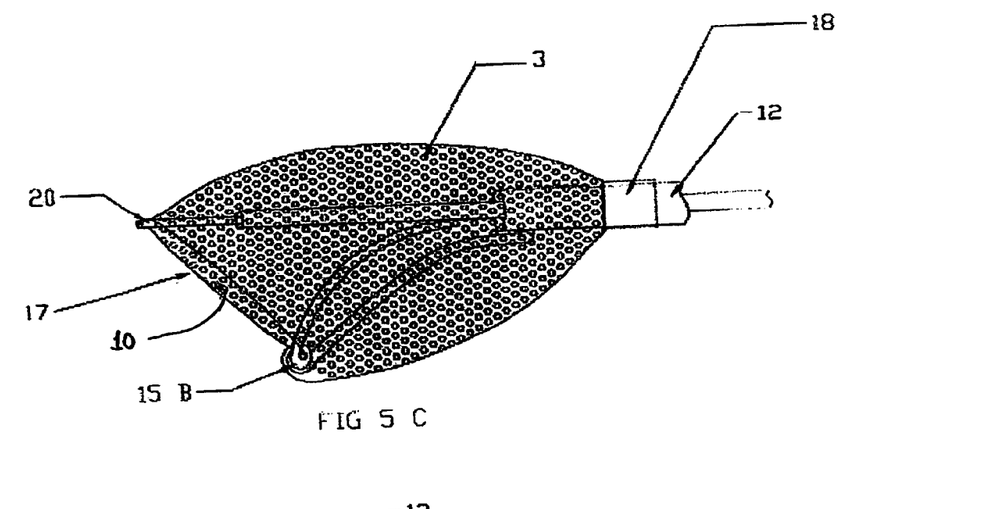
FIG. 5A shows a device having a hoop with a pair of compression and tension struts, configured without a living hinge, in the deployed configuration, with the membrane rendered invisible for clarity.
FIG. 5B shows the device, including the hoop and a pair of compression and tension struts, in the collapsed configuration.
FIG. 5C shows the device in the deployed configuration of FIG. 5A with the membrane made visible.

Another embodiment of this invention is depicted in FIGS. 4 and 5. FIG. 4, similar to FIG. 1, shows a device of the second embodiment deployed at an appropriate location in the aorta. Key labeled parts, numbered as in previous figures, are three tubes 12, 13 and 14; tension and compression struts 7 and 6; a membrane 3, shaded; and a new component, a flexible hoop 17, to which the open proximal end of the filter membrane 3 is attached. It can be seen that the filter 3 is asymmetrically disposed with respect to the catheter tubes. Also labeled is the innominate artery 21 (also called the brachiocephalic trunk), which is the closest to the heart of the arterial branches from the aorta. Positioning the filter "upstream" of this artery, as illustrated here, will provide maximal protection from infarctions caused by debris such as clots and plaque. Entry of the catheter into the circulation through the femoral artery is schematically illustrated at lower left.

The operation of the catheter system of the second embodiment device can be seen more clearly in FIGS. 5A, 5B, and 5C. FIG. 5A illustrates the deployed state, and 5C is the same but with the filter membrane visible. FIG. 5B shows the collapsed state, without membrane. As shown most clearly in FIG. 5A, the catheter system includes a flexible elongated member 12 having a proximal region (not shown) and a distal region. The catheter system includes a filtration membrane 3, shown in FIG. 5C but omitted in FIG. 5A for clarity. The expansion means for the filter typically comprises a compression strut 6, connected to middle tube 13, and a tension strut 7, connected to outer tube 12, as described in the first embodiment. Both struts 6 and 7 are operatively connected to a hoop 17, the other end of which is affixed by any convenient means to inner tube 14, preferably in close approximation to the tip 4. The membrane, as shown in FIG. 5C, is typically connected to tube 12 at its proximal end 18, and to hoop 17 at the open distal end. Wrapping the open end 10 of the membrane around the hoop and gluing or otherwise bonding the membrane to itself is a preferred mode of attachment, since it allows the membrane to slide along the hoop during deployment. The attachment of the hoop 17 to tube 14 may be enhanced by providing a fitting 20. The fitting, or other attachment means, preferably provides for free rotation of the hoop in the fitting. The functional attachment of hoop (17) to the intersection of the struts (6) and (7) is selected from a loop in a continuous strut, a hinge or other locally attached structure comprising a loop, a passage through a strut, and a direct bonding of the loop to a strut or a structure attached to the strut. The attachment region (20) of hoop (17) to tube or wire (14) may be selected from a small loop, a clamp, a clip, and a passage through the tube or wire (14). The junction of struts 6 and 7 is numbered as hinge region 1 5B, but which as illustrated does not require a clearly defined hinge. Instead, the struts here are formed of a single piece of wire, looped to form a small hole to retain hoop 17. Likewise, in this embodiment the proximal ends of the struts are bonded or otherwise connected directly to the outer tube 12 and the middle tube 13, and what might be hinges at 15 and 15A are in this embodiment better described as attachment regions. The bending of both struts in FIG. 5A (compare FIG. 3A) provides the hinge function. However, any of these connections may instead be formed as a hinge, as in FIG. 3.

Deployment of the filter membrane is essentially the same as in the first embodiment. To deploy, the inner tube 14 is moved proximally with respect to middle tube 13, and the outer tube 12 is moved proximally with respect to middle tube 13 to bow the compression strut 6, thereby displacing tension strut 7 laterally. This motion, coupled with the retraction of tube 14, biases the hoop toward a position that is approaching perpendicular to the local axis of the catheter segments. The result is seen in FIG. 4, and more clearly in FIG. 6 below.

Sealing of the filter to the wall of the aorta or other artery can be improved if the hoop 17 is somewhat larger in diameter than the vessel in which it is being positioned. Then, when the hoop 17 is being pushed laterally by the action of the struts 6 and 7, the hoop and its associated membrane 3 will tend to lodge against the arterial wall before the hoop is perpendicular to the catheter axis. This allows a sealing force to be applied.

Turning to FIG. 5B, to retract the filter, the inner tube 14 is extended distally while the struts 6 and 7 are being relaxed by the distal movement of tube 12. Continuing to move tube 14 distally causes a pulling action by hinge 15B (or equivalent) and hoop attachment means 20 on the hoop. This will stretch the hoop into a narrow, substantially closed oval, and the membrane will fold back against the shaft. Optionally, a sheath (not shown) can be positioned over the apparatus distal to tube 12 to retain the components in position during retraction (and during insertion as well).

ALTERNATIVES

As with the first embodiment, tube 14 may contain a guidewire; and/or tube 14 may be replaced with a wire. Middle tube 13 could be replaced with a wire, which, optionally with a joint, would connect to or include strut 6. Strut 7 could be replaced by a wire running proximally to controls. Selection among these options will involve a tradeoff between friction during operation, and simplicity of construction. The presently preferred embodiment is that of FIG. 5, but other options described are viable choices and within the intended scope of the invention. Use of a single pair of struts is sufficient for deployment of the hoop, and is preferred for simplicity, but more than one pair could be used. On the other hand, it is believed that the use of a pair of struts, operating as a compression and a tension strut, is necessary to obtain reliable deployment of the filter, and a distinct improvement over the use of a single, unpaired strut.

Figures 6A, 6B, 6C:
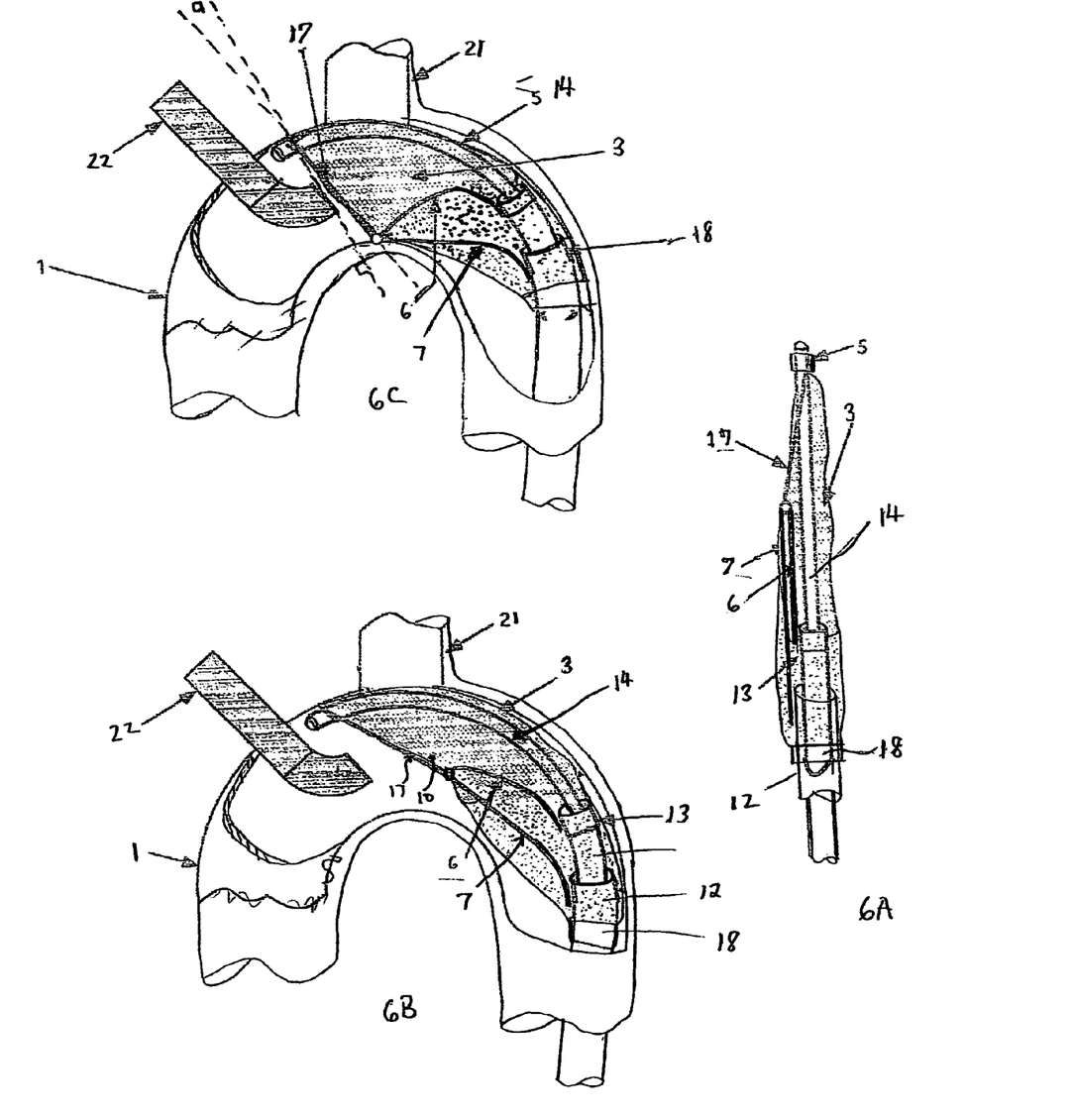
FIG. 6A shows the undeployed state.
FIG. 6B the partially deployed state.
FIG. 6C shows the fully deployed state.

FIG. 6 shows the deployment sequence of the device of FIG. 5 being deployed in an aortic arch, near a cannula 22 from a heart-lung machine. FIG. 6A shows the device in its undeployed state, as in FIG. 5C, but with filter membrane 3 shown. FIG. 6B shows an intermediate state of deployment, with the tension strut 7 pulling the hoop and the compression strut 6 away from the catheter shaft into a semi-deployed position. At this point the compression strut 6 is bowed; tension strut 7 is still straight; and hoop 17 has moved away from inner tube 14 toward the opposite arterial wall. In FIG. 6C, the process is completed, and the hoop 17 has contacted the wall. The hoop 17 is preferably larger in diameter than the expected diameter of the lumen of the aorta. Clearly, if the hoop were smaller, then the seal would be incomplete. Moreover, when the hoop is larger is diameter, even significantly larger, sealing can actually be improved. When a larger-diameter hoop forms a seal in the way shown in FIG. 6c, for example when positioned in the aorta, it will typically make contact with the lumen wall at a deployment angle that is less than perpendicular to the local cylindrical axis of the aortic lumen. This difference from perpendicular is schematically illustrated by the deployment angle a in FIG. 6C. Having the hoop deployed at such an angle does not cause leaks or bypass, but actually tends to improvise the probability of a tight seal. In this state, as illustrated, the hoop and filter have completely blocked the artery, so that all blood, whether from the cannula 22, or, later in the operation, from the heart via the aorta after unclamping, will have to pass through the filter before flowing further into the aorta or into its nearby branches. In particular, the innominate artery 21, which gives rise to one of the carotid arteries, is protected by this design, an improvement over some current commercial designs.

The examples, and the references to figures and figure numbers in the text and in the claims, are intended to aid in the understanding of the invention, and are not intended to limit its scope. Although the invention has been described in some detail by way of illustration and example for the purpose of clarity and understanding, it will be obvious that changes and modifications may be practiced within the scope of the appended claims.

The invention claimed is:

1. An embolic filter comprising a first, outer catheter tube (12) having a distal portion to which is attached a proximal end (18) of an embolic filter membrane (3) and to which tube (12) are also attached one or more tension struts (7); a second, middle catheter tube or wire (13), to which are attached one or more compression struts (6), and wherein each compression strut (6) is also attached to a corresponding tension strut (7); and a third, inner catheter tube or wire (14) to which are connected means connecting the tip region (4) of tube or wire (14) and an open, distal edge (10) of the embolic filter membrane (3), the means providing a way to open or close the open edge (10) of the filter membrane; wherein the embolic filter membrane (3) is deployed into an open position by the deformation of the compression struts (6) and the tension struts (7), when the outer tube (12) and the inner tube or wire (14) are both moved proximally with respect to the middle tube or wire (13).

2. The filter of claim 1, wherein the comprising at least three pairs of compression (6) and tension (7) struts.

3. The filter of claim 2 comprising six to ten pairs of struts.

4. The filter of claim 1, wherein the connecting means comprise a flexible hoop (17) operatively connected to the junction of the struts (6) and (7), and also operatively connected to an attachment device or region (20) of inner tube or wire (14).

5. The filter of claim 4 wherein the hoop (17) with its attached membrane (3) provides a seal between the open end (10) of the filter and the wall of an artery when the hoop (17) is moved into contact with the artery wall by the action of at least one pair of compression (6) and tension (7) struts.

6. The filter of claim 4 wherein the hoop (17) has a diameter greater than the diameter of an aorta (1), thereby providing a seal with the aorta wall when deployed.

7. The filter of claim 4, where the attachment region (20) of hoop (17) to tube or wire (14) is selected to provide for free rotation of the hoop in a fitting, and the functional attachment of hoop (17) to the intersection of the struts (6) and (7) is selected from a loop in a continuous strut, a hinge or other locally attached structure comprising a loop, a passage through a strut, and a direct bonding of the loop to a strut or a structure attached to the strut.

8. The filter of claim 1 wherein one or more of the connections of struts (6) or (7) to each other or to other components is a hinge.

9. The filter of claim 8 wherein the hinge is a living hinge.

* * * * *